(12) United States Patent
Miyawaki (10) Patent No.: US 12,301,970 B2
(45) Date of Patent: May 13, 2025

(54) IMAGE PICKUP UNIT AND ENDOSCOPE

(71) Applicant: OLYMPUS CORPORATION, Tokyo (JP)

(72) Inventor: Takahide Miyawaki, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 69 days.

(21) Appl. No.: 18/378,866

(22) Filed: Oct. 11, 2023

(65) Prior Publication Data

US 2024/0040223 A1    Feb. 1, 2024

Related U.S. Application Data

(63) Continuation of application No. PCT/JP2021/022929, filed on Jun. 16, 2021.

(51) Int. Cl.
| | |
|---|---|
| H04N 23/50 | (2023.01) |
| A61B 1/005 | (2006.01) |
| A61B 1/05 | (2006.01) |
| H04N 23/54 | (2023.01) |
| G02B 23/24 | (2006.01) |

(52) U.S. Cl.
CPC ........... *H04N 23/555* (2023.01); *A61B 1/005* (2013.01); *A61B 1/05* (2013.01); *H04N 23/54* (2023.01); *G02B 23/2484* (2013.01)

(58) Field of Classification Search
None
See application file for complete search history.

(56) References Cited

U.S. PATENT DOCUMENTS

| | | | | |
|---|---|---|---|---|
| 5,021,888 | A * | 6/1991 | Kondou | A61B 1/051 348/76 |
| 10,440,243 | B2 * | 10/2019 | Fujimori | H04N 23/54 |
| 11,647,901 | B2 * | 5/2023 | Yoshida | G02B 23/24 600/101 |
| 2011/0199473 | A1 * | 8/2011 | Kojima | H04N 7/183 257/E23.01 |

(Continued)

FOREIGN PATENT DOCUMENTS

| | | | |
|---|---|---|---|
| CN | 102017622 A * | 4/2011 | ......... A61B 1/00022 |
| JP | 2002-301012 A | 10/2002 | |

(Continued)

OTHER PUBLICATIONS

International Search Report dated Sep. 7, 2021 received in PCT/JP2021/022929.

*Primary Examiner* — Hung Q Dang
(74) *Attorney, Agent, or Firm* — Scully, Scott, Murphy & Presser, P.C.

(57) ABSTRACT

An image pickup unit includes: an image pickup member configured to output an image pickup signal; a sensor; a three-dimensional wiring board including a surface on which the image pickup member is mounted and a different surface on which the sensor is mounted; a signal cable electrically connected to the three-dimensional wiring board; a frame member housing the image pickup member, the sensor, the three-dimensional wiring board, and a distal end portion of the signal cable; a first resin sealing the sensor; and a second resin sealing the distal end portion of the signal cable and having a lower elastic modulus than an elastic modulus of the first resin.

6 Claims, 7 Drawing Sheets

(56) References Cited

U.S. PATENT DOCUMENTS

| | | | | |
|---|---|---|---|---|
| 2011/0249106 A1* | 10/2011 | Makino | ................ | H04N 7/183 |
| | | | | 29/829 |
| 2014/0078287 A1 | 3/2014 | Ichihashi | | |
| 2015/0293343 A1* | 10/2015 | Nagase | .............. | G02B 23/2484 |
| | | | | 348/76 |
| 2019/0021582 A1 | 1/2019 | Shimizu | | |
| 2019/0261839 A1* | 8/2019 | Sakai | .................... | A61B 1/044 |
| 2020/0358931 A1* | 11/2020 | Jenkinson | .............. | G03B 17/08 |

FOREIGN PATENT DOCUMENTS

| | | | | |
|---|---|---|---|---|
| JP | 2006-061326 A | 3/2006 | | |
| JP | 2006-094955 A | 4/2006 | | |
| JP | 4136058 B2 | 8/2008 | | |
| JP | 6574448 B2 | 9/2019 | | |
| WO | 2012/160669 A1 | 11/2012 | | |
| WO | WO-2015107852 A1 * | 7/2015 | ......... | A61B 1/00013 |
| WO | 2017/199776 A1 | 11/2017 | | |
| WO | 2018/061564 A1 | 4/2018 | | |
| WO | WO-2020102119 A2 * | 5/2020 | ............ | G03B 17/55 |
| WO | WO-2022041833 A1 * | 3/2022 | ........... | A61B 1/0008 |

* cited by examiner

IMAGE PICKUP UNIT AND ENDOSCOPE

CROSS REFERENCE TO RELATED APPLICATION

This application is a continuation application of PCT/JP2021/022929 filed on Jun. 16, 2021, the entire contents of which are incorporated herein by this reference.

BACKGROUND OF THE INVENTION

1. Field of the Invention

The invention relates to an image pickup unit with an electronic component and a signal cable connected to a wiring member, and to an endoscope including an image pickup unit with an electronic component and a signal cable connected to a wiring member.

2. Description of the Related Art

Endoscopes are used in medical and industrial fields. Endoscopes with new functions and higher performance have been developed by arranging electronic components other than an image pickup device at a distal end portion of an insertion portion.

Japanese Patent No. 4136058 discloses an endoscope in which a gravity sensor arranged at the distal end portion of the insertion portion is used to detect the direction of gravity in an endoscopic image being observed.

Japanese Patent No. 6574448 discloses an endoscope in which a motion sensor arranged at the distal end portion of the insertion portion is used to control focus by detecting an amount of movement relative to an object.

SUMMARY OF THE INVENTION

In one embodiment, an image pickup unit includes: an image pickup member configured to output an image pickup signal; a first electronic component; a three-dimensional wiring board including a surface on which the image pickup member is mounted and a different surface on which the first electronic component is mounted; a signal cable electrically connected to the three-dimensional wiring board; a frame member housing the image pickup member, the first electronic component, the three-dimensional wiring board, and a distal end portion of the signal cable; first resin sealing the first electronic component; a second resin sealing the distal end portion of the signal cable and having a lower elastic modulus than an elastic modulus of the first resin; a second electronic component configured to process the image pickup signal; a third resin sealing the second electronic component; and a flexible wiring board including a first end portion and a second end portion, in which the signal cable is bonded to the second end portion. The three-dimensional wiring board includes a first wiring board including a first principal surface and a second principal surface on an opposite side from the first principal surface, a second wiring board disposed on the second principal surface and including a third principal surface orthogonal to the second principal surface and a fourth principal surface on an opposite side from the third principal surface, and a third wiring board including a fifth principal surface and a sixth principal surface on an opposite side from the fifth principal surface, in which the fifth principal surface is bonded to the image pickup member and the sixth principal surface is bonded to the first principal surface. The image pickup member is arranged on a side of the first principal surface. The first electronic component is mounted on the third principal surface. The second electronic component is housed in a cavity provided in the sixth principal surface. The first end portion of the flexible wiring board is bonded to the first wiring board. An elastic modulus of the third resin is higher than an elastic modulus of the second resin.

In one embodiment, an endoscope includes an image pickup unit. The image pickup unit includes: an image pickup member configured to output an image pickup signal; a first electronic component; a three-dimensional wiring board including a surface on which the image pickup member is mounted and a different surface on which the first electronic component is mounted; a signal cable electrically connected to the three-dimensional wiring board; a frame member housing the image pickup member, the first electronic component, the three-dimensional wiring board, and a distal end portion of the signal cable; a first resin sealing the first electronic component; a second resin sealing the distal end portion of the signal cable and having a lower elastic modulus than an elastic modulus of the first resin; a second electronic component configured to process the image pickup signal; a third resin sealing the second electronic component; and a flexible wiring board including a first end portion and a second end portion, in which the signal cable is bonded to the second end portion. The three-dimensional wiring board includes a first wiring board including a first principal surface and a second principal surface on an opposite side from the first principal surface, a second wiring board disposed on the second principal surface and including a third principal surface orthogonal to the second principal surface and a fourth principal surface on an opposite side from the third principal surface, and a third wiring board including a fifth principal surface and a sixth principal surface on an opposite side from the fifth principal surface, in which the fifth principal surface is bonded to the image pickup member and the sixth principal surface is bonded to the first principal surface. The image pickup member is arranged on a side of the first principal surface. The first electronic component is mounted on the third principal surface. The second electronic component is housed in a cavity provided in the sixth principal surface. The first end portion of the flexible wiring board is bonded to the first wiring board. An elastic modulus of the third resin is higher than an elastic modulus of the second resin.

DETAILED DESCRIPTION OF THE PREFERRED EMBODIMENTS

First Embodiment

Figure 1:
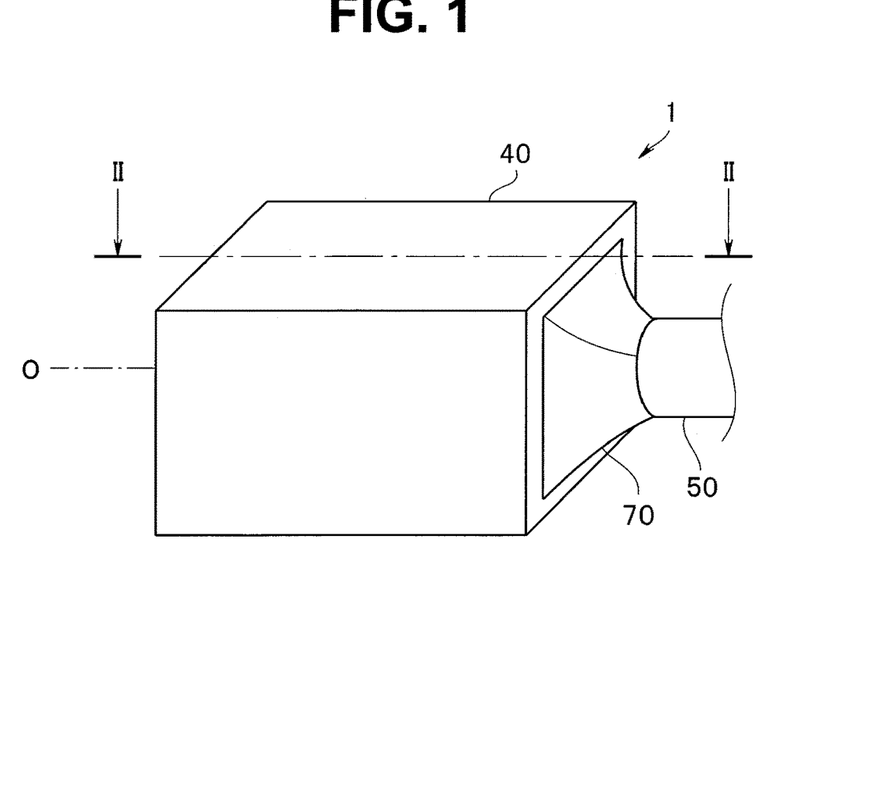
FIG. 1 is a perspective view of an image pickup unit according to a first embodiment.

An image pickup unit 1 according to the present embodiment illustrated in FIGS. 1, 2, and 3 includes: an image pickup portion, namely an image pickup member 10; a three-dimensional wiring board 20; a frame member 40; a first electronic component, namely a movement detection sensor 30 (hereinafter referred to as the "sensor 30"); a signal cable 50; a first resin 61; and a second resin 62.

Note that the drawings based on the embodiment are schematic illustrations. Features such as the relationship between the thickness and width of each portion and the thickness ratios of respective portions are different from the real features. The drawings also include portions where the dimensional relationships and ratios differ from each other. In the drawings, some components are omitted from illustration, and reference signs are not given. For example, in FIG. 3, the first resin 61 and the second resin 62 are not illustrated. The direction in which light is incident is referred to as the "front".

The image pickup member 10 includes a front surface 10SA and a back surface 10SB on the opposite side from the front surface 10SA. The image pickup member 10 includes an image pickup device 11, a cover glass 13, and a transparent resin layer 12 bonding the cover glass 13 to the image pickup device 11. The image pickup device 11 is connected to an electrode 18 on the back surface 10SB by way of through wiring (not illustrated).

The three-dimensional wiring board 20 includes a first wiring board 21 and a second wiring board 22. The first wiring board 21 has a first principal surface 21SA and a second principal surface 21SB on the opposite side from the first principal surface 21SA. The second wiring board 22 has a third principal surface 22SA and a fourth principal surface 22SB on the opposite side from the third principal surface 22SA. The second wiring board 22 is disposed on the second principal surface 21SB such that the third principal surface 22SA and the fourth principal surface 22SB are orthogonal to the second principal surface 21SB. In other words, the first principal surface 21SA and the second principal surface 21SB are orthogonal to an optical axis O, whereas the third principal surface 22SA and the fourth principal surface 22SB are parallel to the optical axis O.

The three-dimensional wiring board 20 is a three-dimensional ceramic wiring board with multiple ceramic wiring layers stacked on top of each other, for example. The ceramic wiring board is fabricated by stacking multiple unfired ceramic sheets, each of which has surface wiring and through wiring, and then firing the stacked ceramic sheets.

The image pickup member 10 is arranged on a side of the first principal surface 21SA, and the electrode 18 of the image pickup member 10 is bonded to an electrode 27 on the first principal surface 21SA of the first wiring board 21 using a first solder 71.

The sensor 30 is a 6-axis inertial measurement unit (IMU) including a 3-axis accelerometer and a 3-axis gyro sensor, for example, in which the accelerometer measures acceleration and the gyro sensor measures angular velocity. The sensor 30 has a movable member such as a cantilever.

The sensor 30 is mounted on the third principal surface 22SA. In other words, an external electrode 38 of the sensor 30 is bonded to an electrode 28 on the third principal surface 22SA using a second solder 72.

In other words, the sensor 30 and the image pickup member 10 are bonded to different surfaces of the three-dimensional wiring board 20.

The signal cable 50 is a composite cable with multiple conducting wires through which the image pickup member 10 or the sensor 30 transmits and receives electrical signals. The signal cable 50 is bonded to an electrode 29 on a notched surface of a side surface 21SS of the second wiring board 22 using a third solder 73.

The frame member 40, the outer shape of which is substantially a rectangular column, houses the image pickup member 10, the sensor 30, the three-dimensional wiring board 20, and the distal end portion of the signal cable 50. For example, the frame member 40 is formed from a copper plate 50 μm to 100 μm thick. The frame member 40 is formed into an angular tube shape, but is not limited to an angular tube and may also be a cylinder. The corners of the inner and outer surfaces of the tube may be chamfered.

The first resin 61 seals the sensor 30. The second resin 62 seals the distal end portion of the signal cable 50.

The first resin 61 has an elastic modulus of 17.6 MPa. The second resin 62 has an elastic modulus of 2.5 MPa. The elastic modulus is the complex elastic modulus (25° C., angular velocity: 1 radian/second) as described in JIS K7244-1 (ISO 6721-1): Plastics-Determination of dynamic mechanical properties. The image pickup unit 1, which is disposed on a rigid distal end portion 90A of an endoscope 9, is subjected to stress with an angular velocity of approximately 1 radian/second during deformation of a bending portion 90B (see FIG. 8).

The first resin 61 is an epoxy resin, but may also be ABS resin or the like. The second resin 62 is a silicone resin, but may also be a polyimide resin, a benzocyclobutene (BCB) resin, or the like.

A signal cable for transmitting and receiving a sensor signal and an image pickup signal or the like is connected to the wiring board on which the sensor is mounted. For example, when an operation of bending the insertion portion is performed, tensile force is applied to the signal cable. If stress is applied to the sensor by way of the wiring board to which the signal cable is connected, the output value from the sensor may fluctuate.

The image pickup unit 1, being provided with the sensor 30, is a high-performance unit. Since the distal end portion of the signal cable 50 is sealed by the second resin 62 with a low elastic modulus, stress applied to the signal cable 50 is relieved by the second resin 62. The sensor 30 is sealed by the first resin 61 with a high elastic modulus. The output values from a sensor with movable parts may fluctuate when stress is applied. However, since the distal end portion of the signal cable 50 is sealed with the second resin 62 and the sensor 30 is sealed by the first resin 61 with a high elastic modulus, stress applied to the signal cable 50 is not readily applied to the sensor 30.

The above-described effect is remarkable when the first resin 61 has an elastic modulus greater than 15 MPa and the second resin 62 has an elastic modulus greater than 0.5 MPa and less than 15 MPa. The upper limit on the elastic modulus of the first resin 61 has no limit in particular, but is 100 MPa, for example. The elastic modulus of the second resin 62 is preferably greater than 1 MPa and less than 10 MPa. The above-described effect is particularly remarkable when the elastic modulus of the first resin 61 is at least 5 times the elastic modulus of the second resin 62.

In the image pickup unit 1, the sensor 30 transmits and receives, by way of the signal cable 50, signals transmitted and received by the image pickup member 10. A dedicated cable for transmitting and receiving signals to and from the sensor 30 is unnecessary to be disposed, thereby simplifying the manufacture of the image pickup unit 1.

According to an embodiment of the invention, a high-performance and highly reliable image pickup unit and a high-performance and highly reliable endoscope can be provided.

The frame member 40, being formed from a metal with a high thermal conductivity, has a high heat dissipation effect. Note that to effectively dissipate heat generated in the image pickup member 10, the inner surface of the front portion of the frame member 40 is preferably in contact with the side surface of the image pickup member 10. The frame member 40 formed from an electric conductor also has an electromagnetic noise shielding effect.

Method of Manufacturing Image Pickup Unit

FIGS. 4A to 4D will be used to briefly describe a method for manufacturing the image pickup unit 1.

Figure 4A:
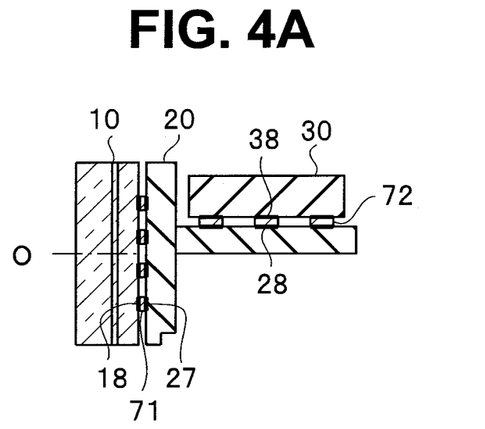
FIG. 4A is a cross section for explaining a method of manufacturing the image pickup unit according to the first embodiment.

As illustrated in FIG. 4A, the electrode 18 of the image pickup member 10 and the electrode 27 of the three-dimensional wiring board 20 are bonded using the first solder 71. The external electrode 38 of the sensor 30 and the electrode 28 of the three-dimensional wiring board 20 are bonded using the second solder 72.

The image pickup device 11 of the image pickup member 10 is a front-illuminated image sensor or a back-illuminated image sensor. One or more semiconductor devices that process image pickup signals may be stacked on the back surface of the image pickup device 11, and the electrode 18 may be disposed on the back surface of the semiconductor device, that is, the back surface 10SB of the image pickup member 10.

The three-dimensional wiring board 20 may include multiple glass epoxy wiring boards bonded together, or may be a molded interconnect device in which the first and second wiring boards are molded as a single piece.

The sensor 30 is manufactured using MEMS technology, in which numerous movable parts such as cantilevers, piezoelectric elements that detect changes in the movable parts, and the like are fabricated on a silicon wafer at the same time in a single batch. The sensor 30 may be an accelerometer or a gyro sensor, for example. Note that the first electronic component is not limited to the sensor 30. However, the effect of the invention is particularly remarkable in the case in which the electronic component is a sensor with movable parts for detecting a physical quantity, and which is particularly susceptible to outside air.

Note that second electronic components 31 such as chip capacitors may also be mounted on, for example, the fourth principal surface 22SB of the three-dimensional wiring board 20.

Figure 4B:
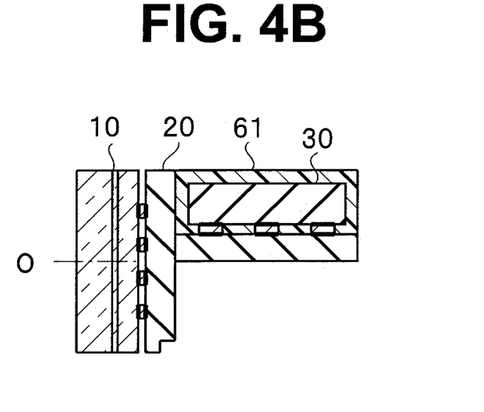
FIG. 4B is a cross section for explaining the method of manufacturing the image pickup unit according to the first embodiment.

As illustrated in FIG. 4B, the sensor 30 is sealed by the first resin 61.

Figure 4C:
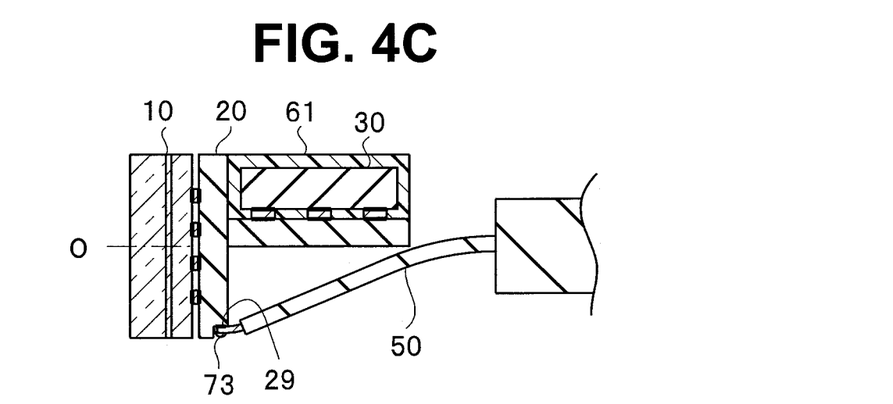
FIG. 4C is a cross section for explaining the method of manufacturing the image pickup unit according to the first embodiment.

As illustrated in FIG. 4C, the signal cable 50 is bonded to the electrode 29 on the notched surface of the side surface 21SS of the second wiring board 22 using the third solder 73.

To prevent re-melting of an already soldered joint, the melting point of the third solder 73 is preferably at or below the melting points of the first solder 71 and the second solder 72, particularly preferably 10° C. or more below the melting points of the first solder 71 and the second solder 72. The notch in the side surface 21SS is deep enough that the soldered signal cable 50 does not protrude from the side surface 21SS.

Figure 4D:
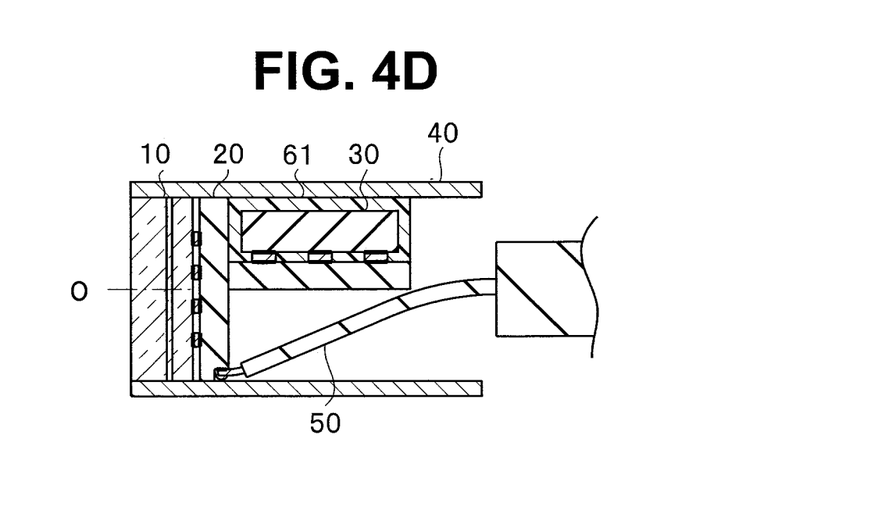
FIG. 4D is a cross section for explaining the method of manufacturing the image pickup unit according to the first embodiment.

As illustrated in FIG. 4D, the image pickup member 10, the sensor 30, and the signal cable 50 are bonded to respectively different surfaces of the three-dimensional wiring board 20, and the three-dimensional wiring board 20 is housed in the frame member 40. In other words, the hollow portion of the frame member 40 is of a size that can accommodate the three-dimensional wiring board 20. In the case in which an optical system is disposed on the front surface 10SA of the image pickup member 10, at least a portion of the optical system may be housed in the frame member 40.

Figure 2:
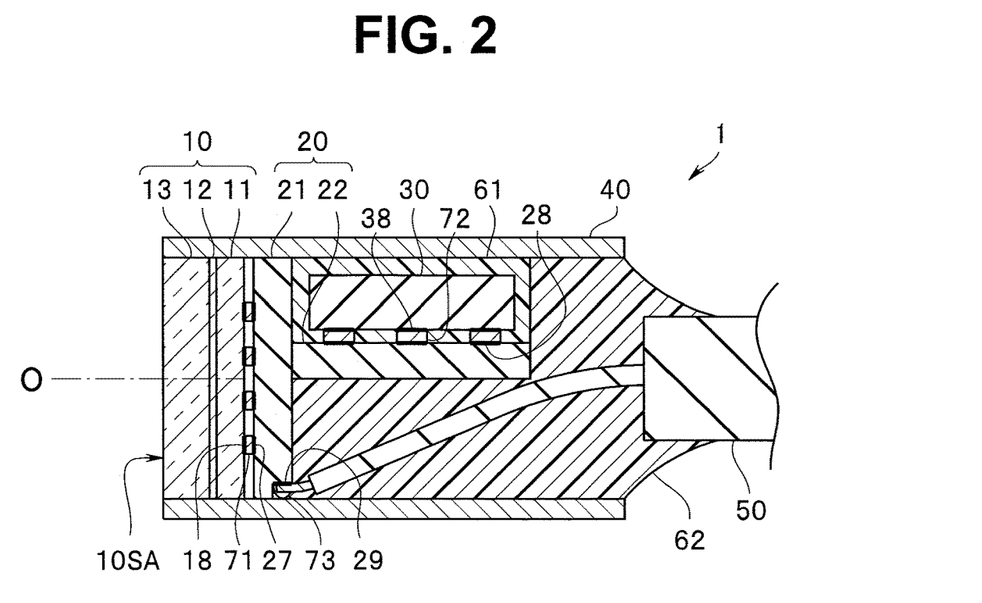
FIG. 2 is a cross section along line II-II in FIG. 1.
Figure 3:
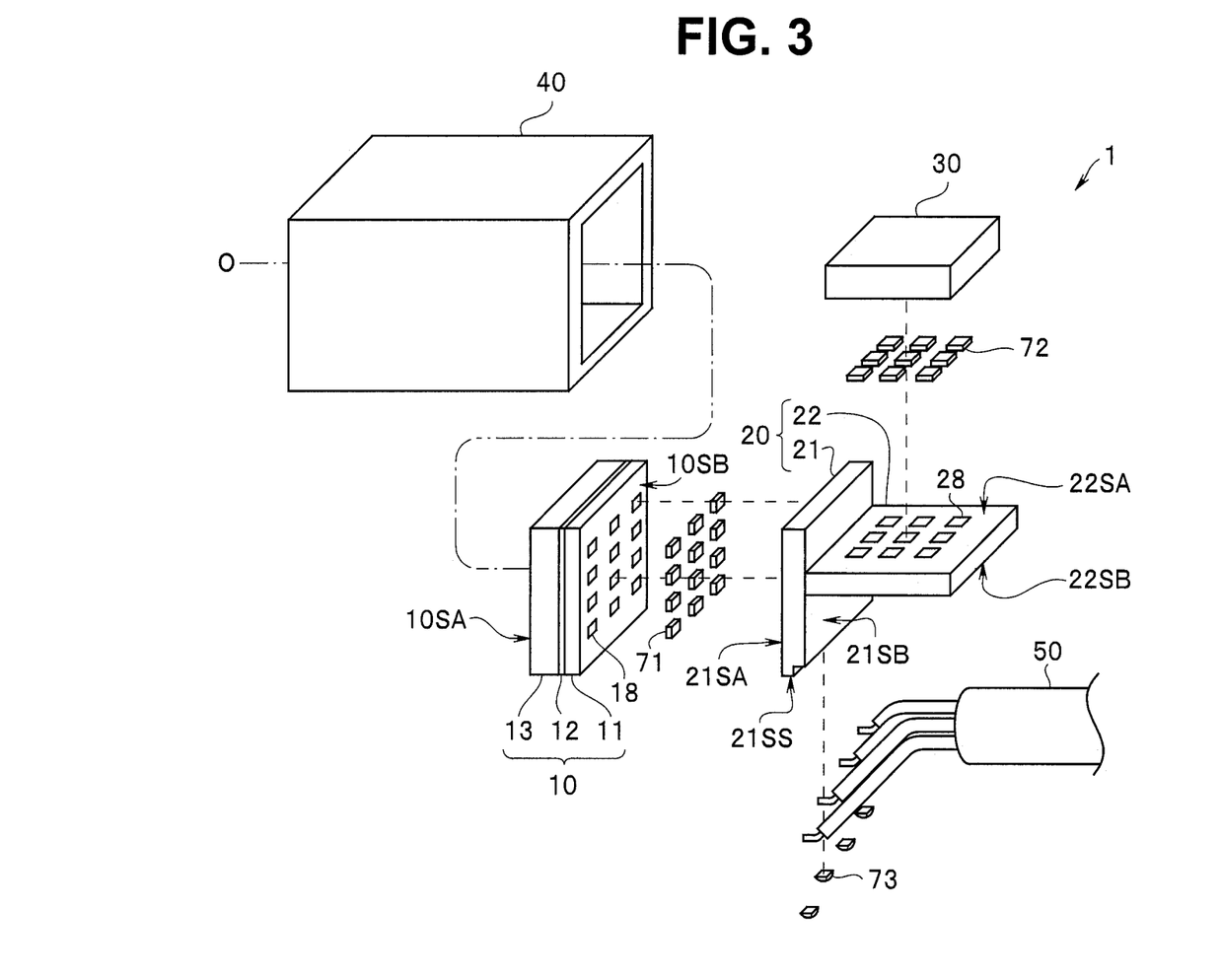
FIG. 3 is an exploded perspective view of the image pickup unit according to the first embodiment.

The hollow portion of the frame member 40 with the distal end portion of the signal cable 50 placed inside is then filled with the second resin 62, thus completing the image pickup unit 1 illustrated in FIG. 2.

Second Embodiment

Figure 5:
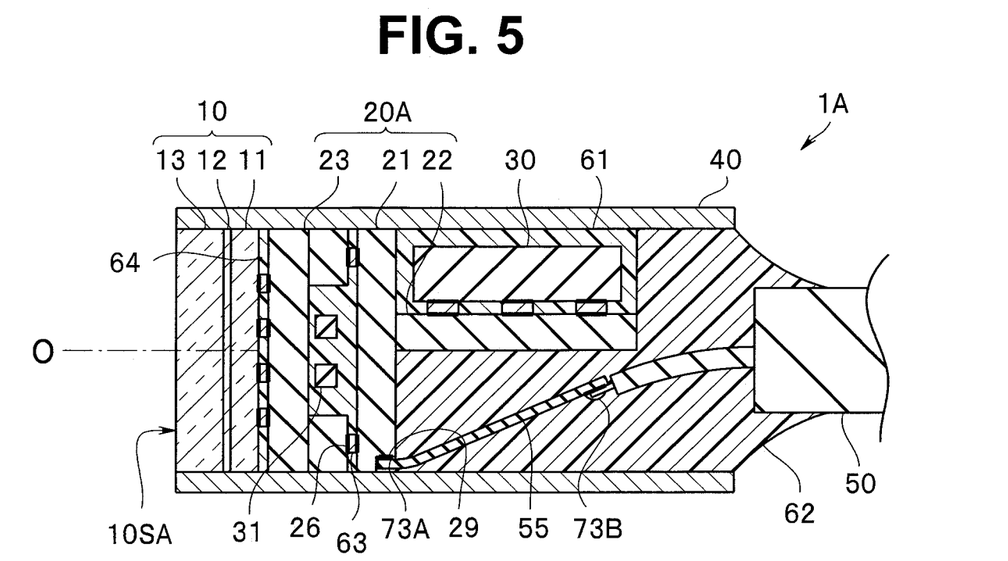
FIG. 5 is a cross section of an image pickup unit according to a second embodiment.
Figure 6:
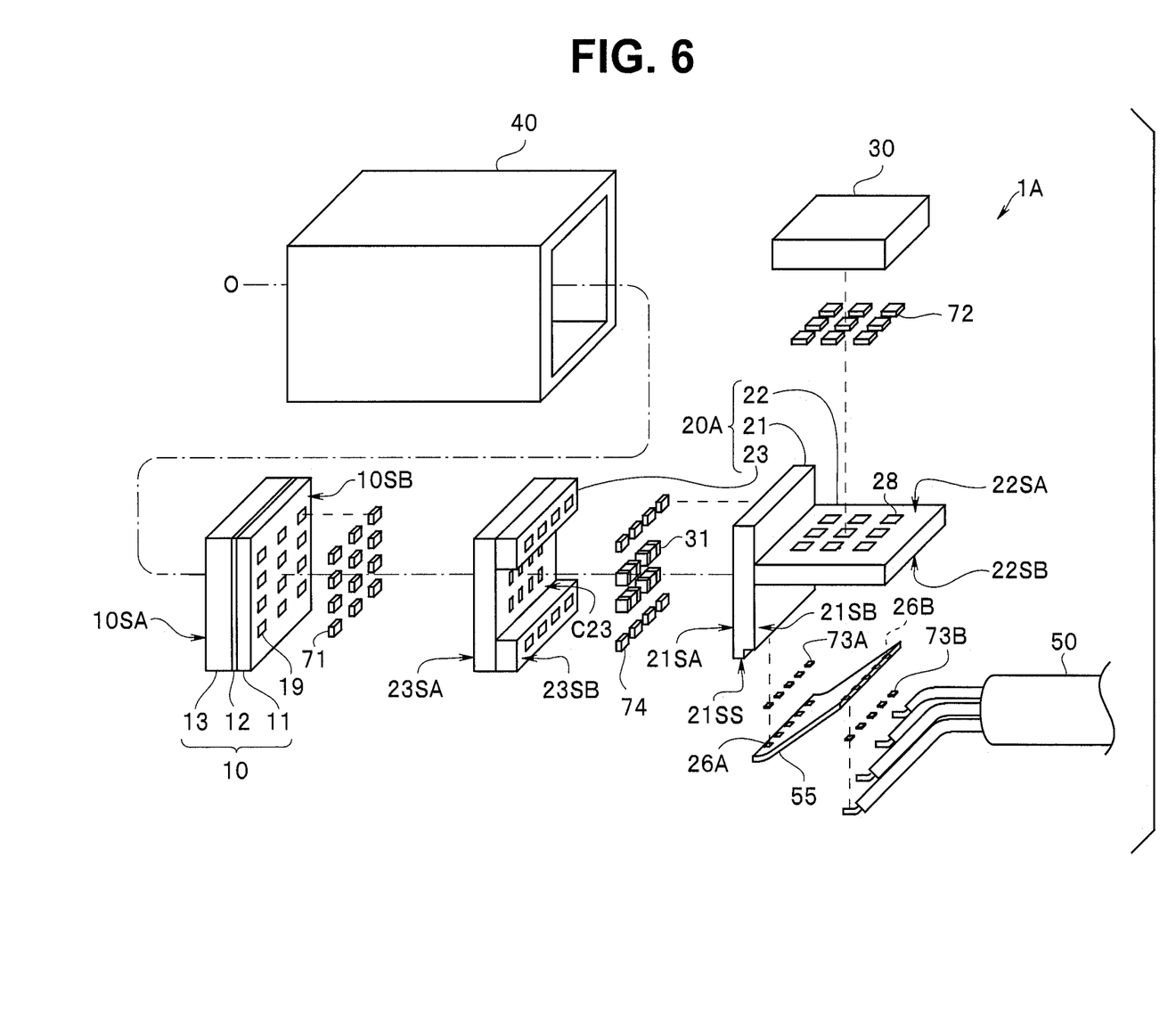
FIG. 6 is an exploded perspective view of the image pickup unit according to the second embodiment.

An image pickup unit 1A according to a second embodiment resembles the image pickup unit 1 and has the same effects, and therefore components having the same functions are denoted with the same reference signs, and description of the components is omitted.

The image pickup unit 1A illustrated in FIGS. 5 and 6 includes the configuration of the image pickup unit 1 with the addition of second electronic components 31, a flexible wiring board 55, and a third resin 63.

A three-dimensional wiring board 20A includes the configuration of the three-dimensional wiring board 20 with the addition of a third wiring board 23. The third wiring board 23 has a fifth principal surface 23SA and a sixth principal surface 23SB on the opposite side from the fifth principal surface 23SA. An electrode 26 on the sixth principal surface 23SB and the electrode 27 on the first principal surface 21SA of the first wiring board 21 are bonded using a fourth solder 74.

A cavity (groove) C23 with openings on two sides is formed on the sixth principal surface 23SB of the third wiring board 23. The second electronic components 31 such as chip capacitors, that process image pickup signals are housed in the cavity (groove) C23.

The flexible wiring board 55 has a first end portion where an electrode 26A is disposed and a second end portion where an electrode 26B is disposed. The electrodes 26A and 26B are connected by way of wiring.

The electrode 26A at the first end portion is bonded to the electrode 29 on the notched surface of the side surface 21SS of the first wiring board 21 using a third solder 73A. The signal cable 50 is bonded to the electrode 26B at the second end portion using a third solder 73B.

To prevent re-melting of an already soldered joint, the melting point of the fourth solder 74 is preferably 10° C. or more above the melting points of the first solder 71, the second solder 72, and the third solders 73A, 73B.

The third resin 63 disposed between the first principal surface 21SA of the first wiring board 21 and the sixth principal surface 23SB of the third wiring board 23 seals the second electronic component 31. An elastic modulus of the third resin 63 is higher than an elastic modulus of the second resin 62.

A fourth resin 64 is disposed between the back surface 10SB of the image pickup member 10 and the fifth principal surface 23SA of the third wiring board 23. The elastic modulus of the fourth resin 64 is higher than the elastic modulus of the second resin 62.

Since the second electronic component 31 is disposed on the three-dimensional wiring board 20A, the image pickup unit 1A has higher performance than the image pickup unit 1. Since the signal cable 50 is electrically connected to the three-dimensional wiring board 20A by way of the flexible wiring board 55, the image pickup unit 1A is easy to manufacture.

Modification of Second Embodiment

Figure 7:
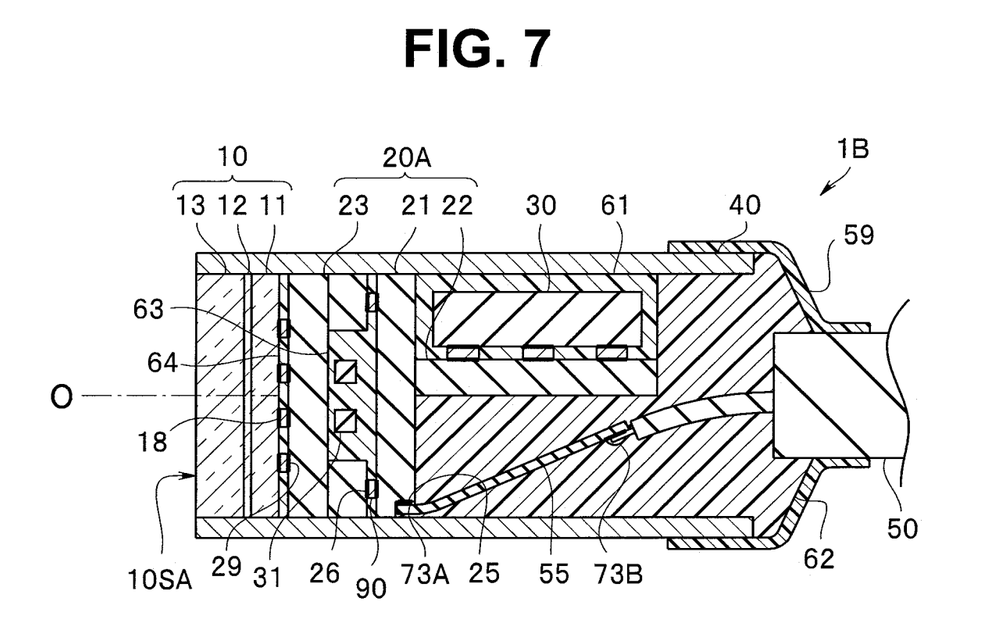
FIG. 7 is a cross section of an image pickup unit according to a modification of the second embodiment.

An image pickup unit 1B according to the present modification resembles the image pickup unit 1A and has the same effects, and therefore components having the same functions are denoted with the same reference signs, and description of the components is omitted.

As illustrated in FIG. 7, the image pickup unit 1B further includes a resin tube 59 connecting the frame member 40 and the signal cable 50. The second resin 62 is also disposed inside the resin tube 59.

When the gel-like second resin 62 is disposed, the second resin 62 does not spread to the surrounding area, and thus the image pickup unit 1B is easy to manufacture.

Third Embodiment

Figure 8:
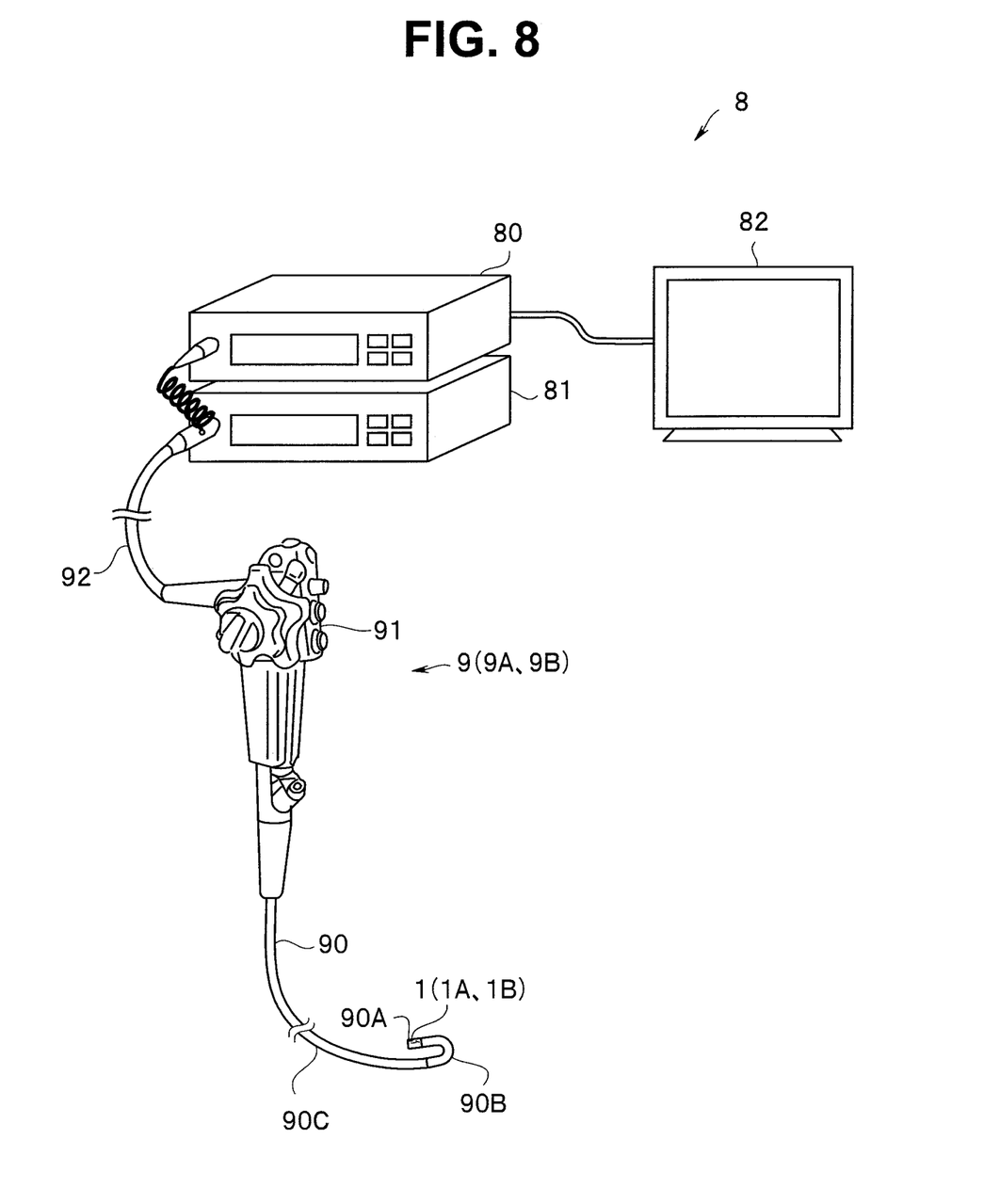
FIG. 8 is an external view of an endoscope according to a third embodiment.

As illustrated in FIG. 8, an endoscope system 8 including the endoscope 9 according to the present embodiment includes a processor 80, a light source device 81, and a monitor 82. The endoscope 9 has an insertion portion 90 that is inserted into a body cavity of a subject, with which the endoscope 9 picks up an image inside the body of the subject and outputs an image pickup signal.

An operation portion 91 provided with various buttons for operating the endoscope 9 is disposed on a proximal end portion of the insertion portion 90 of the endoscope 9. The insertion portion 90 has a rigid distal end portion 90A where the image pickup unit 1 (1A, 1B) is disposed, a freely bendable bending portion 90B provided continuously to the proximal end portion of the rigid distal end portion 90A, and an elongate flexible portion 90C connected to the proximal end portion of the bending portion 90B. The bending portion 90B bends in response to the operation of the operation portion 91.

A universal cord 92 provided so as to extend from the operation portion 91 is connected to the processor 80 and the light source device 81.

The processor 80 controls the endoscope system 8 as a whole, and performs signal processing on an image pickup signal outputted by the image pickup unit 1 and outputs the signal processing result as an image signal. The monitor 82 displays the image signal outputted by the processor 80.

The light source device 81 includes a white LED, for example. Illuminating light emitted by the light source device 81 is guided to the rigid distal end portion 90A by way of a light guide (not illustrated) inserted into an universal cord 92 and the insertion portion 90, and illuminates an object.

The endoscope 9 includes the image pickup unit 1, 1A, 1B, and therefore has high performance and stable operation.

Note that the endoscope 9 is a flexible endoscope for medical use, but an endoscope according to a different embodiment may be an endoscope for industrial use or a rigid endoscope including a rigid straight pipe in place of the flexible portion 90C.

The invention is not limited to the embodiments and the like described above, and various modifications, alterations, and the like are possible without changing the gist of the invention.

What is claimed is:

1. An image pickup unit comprising:
   an image pickup member configured to output an image pickup signal;
   a first electronic component;
   a three-dimensional wiring board including a surface on which the image pickup member is mounted and a different surface on which the first electronic component is mounted;
   a signal cable electrically connected to the three-dimensional wiring board;
   a frame member housing the image pickup member, the first electronic component, the three-dimensional wiring board, and a distal end portion of the signal cable;
   a first resin sealing the first electronic component;
   a second resin sealing the distal end portion of the signal cable and having a lower elastic modulus than an elastic modulus of the first resin;
   a second electronic component configured to process the image pickup signal;
   a third resin sealing the second electronic component; and
   a flexible wiring board including a first end portion and a second end portion, the signal cable being bonded to the second end portion, wherein
   the three-dimensional wiring board includes a first wiring board including a first principal surface and a second principal surface on an opposite side from the first principal surface, a second wiring board disposed on the second principal surface and including a third principal surface orthogonal to the second principal surface and a fourth principal surface on an opposite side from the third principal surface, and a third wiring board including a fifth principal surface and a sixth principal surface on an opposite side from the fifth principal surface, the fifth principal surface being bonded to the image pickup member and the sixth principal surface being bonded to the first principal surface,
   the image pickup member is arranged on a side of the first principal surface,
   the first electronic component is mounted on the third principal surface,
   the second electronic component is housed in a cavity provided in the sixth principal surface,
   the first end portion of the flexible wiring board is bonded to the first wiring board, and
   an elastic modulus of the third resin is higher than an elastic modulus of the second resin.

2. The image pickup unit according to claim 1, wherein the first electronic component is a movement detection sensor including a movable member.

3. The image pickup unit according to claim 2, wherein the first resin has an elastic modulus greater than 15 MPa, and
the second resin has an elastic modulus greater than 0.5 MPa and less than 15 MPa.

4. The image pickup unit according to claim 3, wherein the elastic modulus of the first resin is at least 5 times higher than the elastic modulus of the second resin.

5. The image pickup unit according to claim 1, further comprising
   a resin tube connecting the frame member and the signal cable, wherein
   the resin tube is also filled with the second resin.

6. An endoscope including a rigid distal end portion and a bending portion,
   an image pickup unit being arranged on the rigid distal end portion, the image pickup unit comprising:
   an image pickup member configured to output an image pickup signal;
   a first electronic component;
   a three-dimensional wiring board including a surface on which the image pickup member is mounted and a different surface on which the first electronic component is mounted;
   a signal cable electrically connected to the three-dimensional wiring board;
   a frame member housing the image pickup member, the first electronic component, the three-dimensional wiring board, and a distal end portion of the signal cable;
   a first resin sealing the first electronic component;
   a second resin sealing the distal end portion of the signal cable and having a lower elastic modulus than an elastic modulus of the first resin;
   a second electronic component configured to process the image pickup signal;
   a third resin sealing the second electronic component; and
   a flexible wiring board including a first end portion and a second end portion, the signal cable being bonded to the second end portion, wherein
   the three-dimensional wiring board includes a first wiring board including a first principal surface and a second principal surface on an opposite side from the first principal surface, a second wiring board disposed on the second principal surface and including a third principal surface orthogonal to the second principal surface and a fourth principal surface on an opposite side from the third principal surface, and a third wiring board including a fifth principal surface and a sixth principal surface on an opposite side from the fifth principal surface, the fifth principal surface being bonded to the image pickup member and the sixth principal surface being bonded to the first principal surface,
   the image pickup member is arranged on a side of the first principal surface,
   the first electronic component is mounted on the third principal surface,
   the second electronic component is housed in a cavity provided in the sixth principal surface,
   the first end portion of the flexible wiring board is bonded to the first wiring board, and
   an elastic modulus of the third resin is higher than an elastic modulus of the second resin.

* * * * *